(12) United States Patent
Ueki (10) Patent No.: US 7,809,110 B2
(45) Date of Patent: Oct. 5, 2010

(54) X-RAY IMAGING DEVICE (75) Inventor: Hironori Ueki, Hachioji (JP)

(73) Assignee: Hitachi Medical Corporation, Tokyo (JP)

( * ) Notice: Subject to any disclaimer, the term of this patent is extended or adjusted under 35 U.S.C. 154(b) by 682 days.

(21) Appl. No.: 11/720,942

(22) PCT Filed: Jan. 5, 2006

(86) PCT No.: PCT/JP2006/300031

§ 371 (c)(1),
(2), (4) Date: Jun. 6, 2007

(87) PCT Pub. No.: WO2006/075546

PCT Pub. Date: Jul. 20, 2006

(65) Prior Publication Data

US 2010/0046709 A1    Feb. 25, 2010

(30) Foreign Application Priority Data

Jan. 11, 2005  (JP)  ............................. 2005-003412

(51) Int. Cl.
*H05G 1/64*  (2006.01)
*H05G 1/60*  (2006.01)
(52) U.S. Cl. .......................................... 378/98; 378/19
(58) Field of Classification Search ............. 378/7, 378/19, 98.8, 146–154
See application file for complete search history.

(56) References Cited

U.S. PATENT DOCUMENTS 7,245,776 B2 *  7/2007  Matsuura ..................... 382/240

FOREIGN PATENT DOCUMENTS

| JP | 60-127650 | 7/1985 |
| JP | 02-147883 | 6/1990 |
| JP | 08-252248 | 10/1996 |
| JP | 2000-350723 | 12/2000 |
| JP | 2002-000595 | 1/2002 |
| JP | 2004-325126 | 11/2004 |

* cited by examiner

*Primary Examiner*—Irakli Kiknadze
(74) *Attorney, Agent, or Firm*—Antonelli, Terry, Stout & Kraus, LLP.

(57) ABSTRACT

An X-ray detection technology capable of suppressing a decrease in a signal-to-noise ratio derived from external noise even in a case where it is hard to intercept electromagnetic-wave noise, and offering a wide dynamic range is realized, and an X-ray imaging device utilizing the technology is provided. An electromagnetic-wave noise signal to be mixed in a signal detected by an X-ray detector 2 is inferred from electromagnetic-wave noise signals measured by reference detectors 10A and 10B according to the method of least squares. Noise removal calculation is performed in order to minimize the decrease in a signal-to-noise ratio derived from the electromagnetic-wave noise.

10 Claims, 9 Drawing Sheets

X-RAY IMAGING DEVICE

TECHNICAL FIELD

The present invention relates to X-ray imaging technologies to be employed in diagnostic imaging or industrial inspection.

BACKGROUND ART

X-ray imaging devices are widely used in the fields of diagnostic imaging and industrial inspection alike. For measurement of an X-ray signal that exponentially decays in a subject, a measurement system that offers a wide dynamic range is needed. In general, the maximum value of the dynamic range is determined with a maximum output capacity given by an X-ray source and a maximum permissible dose of a subject. Based on a maximum incident dose attained under these conditions, the maximum detectable capacity of an X-ray detector is designed. On the other hand, the minimum value of the dynamic range is determined with noise caused by an X-ray detector. For expansion of the dynamic range, minimization of noise is essential.

The noise includes circuit noise (internal noise) occurring in the detector and noise derived from mixing of electromagnetic waves coming outside the detector (external noise). In particular, since an X-ray imaging device includes numerous sources of intensive electromagnetic waves such as an X-ray generator, a power source for the X-ray generator, a mechanical system, and others, the latter external noise often becomes a major factor of a decrease in the dynamic range. Therefore, an electromagnetic shield has been used to shield the X-ray detector or any other measures have been taken (refer to, for example, patent documents 1 and 2).

Patent document 1: Japanese Patent Application Laid-Open Publication No. 2002-595

Patent document 2: Japanese Patent Application Laid-Open Publication No. 2004-325126

DISCLOSURE OF THE INVENTION

Problems to be Solved by the Invention

In efforts to reduce external noise, X-ray detectors generally have the flanks and backs thereof shielded with metallic plates. However, the input surface of the X-ray detector is not shielded in order to avoid decay of X-rays caused by an electromagnetic shield, or covered with a relatively thin shield. This poses a problem in that electromagnetic-wave noise is not fully intercepted and that it is hard to reduce the external noise.

Means for Solving the Problem

An object of the present invention is to realize an X-ray detection technology that provides a wide dynamic range while suppressing a decrease in a signal-to-noise ratio derived from external noise even in a case where it is hard to intercept electromagnetic-wave noise, and to provide an X-ray imaging device utilizing the X-ray detection technology.

In order to accomplish the foregoing object, an X-ray imaging device in accordance with the present invention is designed to have features described below.

(1) An X-ray imaging device having a means for generating X-rays, a collimator that limits an X-irradiation range, and an X-ray detection means for detecting an X-rays-transmitted image of a subject includes: N (where $1 \leq N$ is established) pieces of reference signal detection means arranged in a non X-irradiation region; a first calculation means for approximating a noise signal $p(t)$ (where t denotes time), which is detected by the X-ray detection means with X-irradiation to the X-ray detection means substantially intercepted by the collimator, using a linear sum, $p'(t)=\alpha_1 q_1(t)+\alpha_2 q_2(t)+$, etc., $+\alpha_N q_N(t)$, of N reference signals $q(t)$ (where n ranges from 1 to N) detected by each of the pieces of reference signal detection means, and calculating weight coefficients $\alpha_n$ (where n ranges from 1 to N) that minimize a mean squared error of the approximate value; a storage means in which the values of the weight coefficients $\alpha_n$ calculated by the first calculation means are stored; and a second calculation means for calculating a noise removal signal $f(t)-p'(t)$ using the signal $f(t)$ and reference signals $q_n(t)$, which are measured by the X-ray detection means and the pieces of reference signal detection means respectively, and the weight coefficients $\alpha_n$ stored in the storage means.

Consequently, even when electromagnetic noise enters the X-ray detection means, the reference signals detected by the pieces of reference signal detection means are used to remove external noise from a measured signal. Eventually, a signal-to-noise ratio attained in the X-ray detector improves.

(2) In the X-ray imaging device set forth in (1), the pieces of reference signal detection means are realized with part of multiple detection elements constituting the X-ray detection means.

Consequently, since external detectors need not be procured as the pieces of reference signal detection means, the structure of the X-ray detector can be simplified and a cost of manufacture can be reduced.

(3) The X-ray imaging device set forth in (1) or (2) includes first and second collimators that are interposed between the X-ray generation means and an subject or between the subject and the pieces of reference signal detection means, and that substantially intercept X-irradiation to the pieces of reference signal detection means.

Consequently, a wasted radiation dose of a subject can be reduced owing to the first collimator, and incidence of scattered X-rays, which are generated in the subject, on the pieces of reference signal detection means can be prevented by the second collimator. Eventually, the precision in measurement of electromagnetic noise by the pieces of reference signal detection means improves.

In the X-ray imaging device set forth in (1), (2), or (3), the pieces of reference signal detection means each include M (where N<M is established) reference detection elements. The N reference signals $q_n(t)$ are signals detected by N reference detection elements designated in advance.

Consequently, the number of reference signal detection elements that presumably play a pivotal role in reducing external noise which varies depending on a use environment can be limited. Eventually, the number of arithmetic operations required for noise removal calculation can be decreased and a calculation time can be shortened.

(5) In the X-ray imaging device set forth in (4), part or all of N reference signals $q_n(t)$ are each a sum of signals detected by multiple reference detection elements.

Consequently, circuit noise occurring in the reference detection element can be reduced, and an increase in internal noise derived from noise removing calculation can be reduced.

(6) In the X-ray imaging device set forth in (4) or (5), the combination of N reference detection elements to be designated can be modified relative to each of the detection elements constituting the X-ray detection means.

Consequently, an optimal combination of reference detection elements can be selected relative to each of the detection elements constituting the X-ray detection means. Eventually, the precision in removing external noise improves.

(7) In the X-ray imaging device set forth in (6), a combination of N reference detection elements that are located at the shortest distance from one another is designated relative to each of the detection elements constituting the X-ray detection means.

Consequently, the most influential reference detection elements can be selected relative to each of the detection elements constituting the X-ray detection means. Eventually, the precision in removing external noise improves.

Effect of the Invention

According to the present invention, an X-ray detection technology capable of suppressing a decrease in a signal-to-noise ratio derived from external noise even when it is hard to intercept electromagnetic-wave noise, and offering a wide dynamic range can be realized, and an X-ray imaging device utilizing the X-ray detection technology can be provided.

BEST MODE FOR CARRYING OUT THE INVENTION

Prior to a description of embodiments of the present invention, the principles of an external noise reduction method implemented in the present invention will be described in conjunction with FIG. 15.

Figure 15:
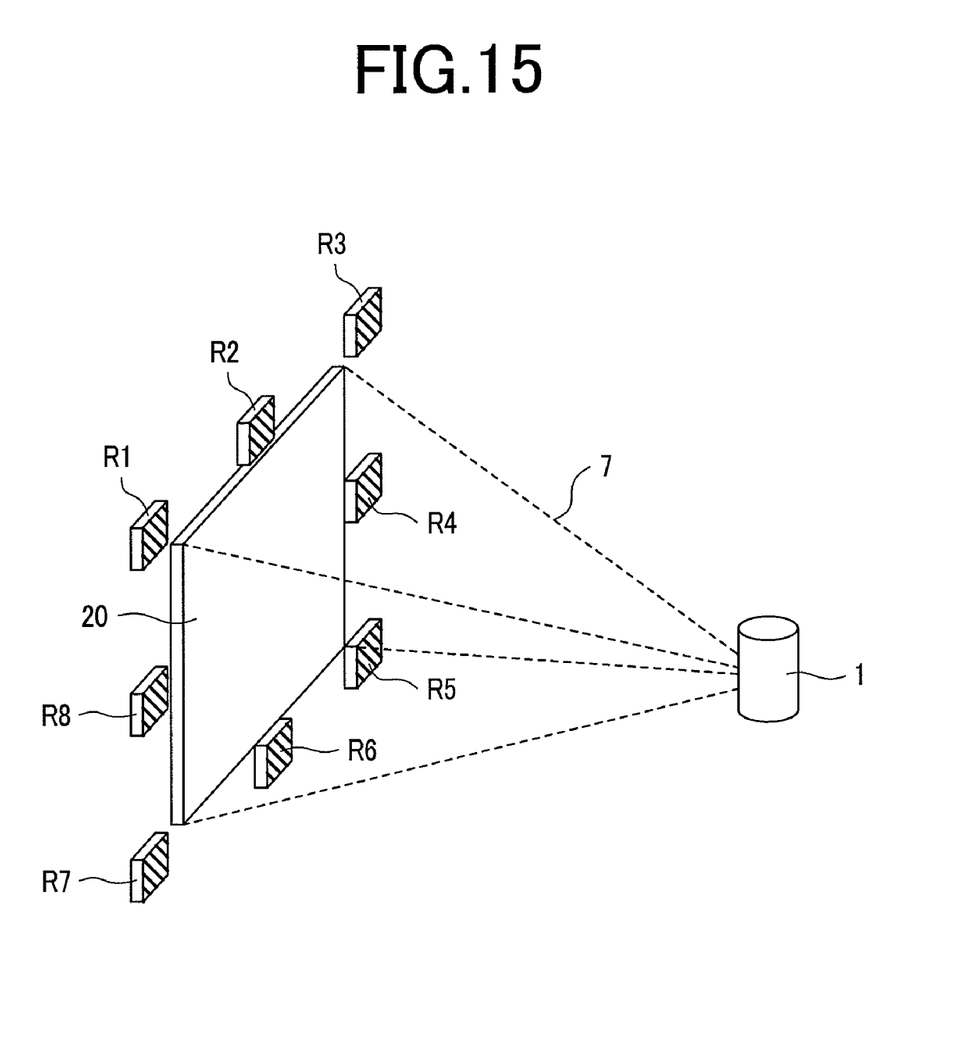

FIG. 15 shows the typical configuration of an X-ray imaging device to which the present invention is adapted. The X-ray imaging device includes an X-ray source 1, an X-ray detector 20, and reference detectors R1 to R8. X-rays radiated from the X-ray source 1 have the irradiation range 7 thereof confined to the detecting surface of the X-ray detector 20 by a known collimator that is not shown. X-rays are not irradiated directly to the reference detectors R1 to R8. Moreover, a known collimator that is not shown is disposed on each of the faces of the reference detectors R1 to R8 for fear scattered X-rays generated in a subject may fall on the reference detectors. Electromagnetic-wave noise generated externally enters the X-ray detector 20 and reference detectors R1 to R8 alike, and is detected as external noise over various signal lines, a power line, and a ground line in the detectors. Numerous sources are conceivable as electromagnetic-wave noise sources. The X-ray detector 20 and reference detectors R1 to R8 measure the external noise as noises of different intensities.

On the assumption that the X-ray imaging device has the foregoing configuration, a method of removing external noise will be described below. Although eight reference detectors R1 to R8 are shown in FIG. 15 to be included in the X-ray imaging device, the number of reference detectors shall be generally N ($1 \leq N$) hereinafter. Now, p(t) shall denote an external noise signal to be detected by a certain detection element (pixel) included in the X-ray detector 20 at a certain time instant t. The external noise signal p(t) can be acquired by performing radiography with X-rays, which fall on the X-ray detector 20, intercepted by a collimator that is not shown. Moreover, $q_n(t)$ (where n ranges from 1 to N) shall denote external noise (a reference signal) detected by each reference detector at the same time. Assuming that the X-ray detector 20 and each of the reference detectors measure electromagnetic-wave noise caused by the same source, the signal p(t) correlates with the signals $q_n(t)$ to some extent. Consequently, the signal p(t) is approximated to the linear sum of the signals $q_n(t)$ according to the following formula:

[Formula 1]

$$p(t) \cong p'(t) \sum_{n=1}^{N} \alpha_n q_n(t) \quad (1)$$

where $\alpha_n$ denotes approximation coefficients (weight coefficients). Using the method of least squares, the optimal value of each approximation coefficient $\alpha_n$ is determined as a value minimizing a mean squared error between the value p(t) and the approximate value p'(t). Namely, the following equation is established:

[Formula 2]

$$\frac{\partial}{\partial \alpha_K} \int \left\{ p(t) - \sum_{n=1}^{N} \alpha_n q_n(t) \right\}^2 dt = 0 \quad (2)$$

The formula 2 is solved by changing the approximation coefficients $\alpha_n$ to be assigned to the formula 2, whereby the following formula is established:

[Formula 3]

$$\begin{bmatrix} \sigma(p, q_1) \\ \sigma(p, q_2) \\ \vdots \\ \sigma(p, q_N) \end{bmatrix} = \begin{bmatrix} \sigma(q_1, q_1) & \sigma(q_1, q_2) & \cdots & \sigma(q_1, q_N) \\ \sigma(q_2, q_1) & \sigma(q_2, q_2) & \cdots & \sigma(q_2, q_N) \\ \vdots & \vdots & \ddots & \vdots \\ \sigma(q_N, q_1) & \sigma(q_N, q_2) & \cdots & \sigma(q_N, q_N) \end{bmatrix} \begin{bmatrix} \alpha_1 \\ \alpha_2 \\ \vdots \\ \alpha_N \end{bmatrix} \quad (3)$$

where a function $\sigma$ is a cross-correlation function and defined as the following formula:

[Formula 4]

$$s(f_1, f_2) = \int f_1(t) f_2(t) dt \quad (4)$$

Assuming that A denotes the matrix in the left side of the formula 3, B denotes the matrix in the first term in the right side of the formula 3, and C denotes the matrix in the second term in the right side thereof, the matrix C having optimal approximation coefficients as elements thereof is calculated as $C=B^{-1}A$. Using the foregoing procedure, the optimal approximation coefficients can be worked out prior to radiography. During radiography, the X-ray detector 20 and the reference detectors measure an image signal f(t) and external noise $q_n(t)$ respectively. At this time, the external noise component of the radiographic signal f(t) can be estimated according to the formula 1. Consequently, a noise removal signal g(t) can be calculated using the following formula:

[Formula 5]

$$g(t) = f(t) - \sum_{n=1}^{N} \alpha_n q_n(t) \quad (5)$$

The foregoing noise removing method can be implemented in X-ray imaging devices intended for various usages. Now, the embodiments of the present invention will be described below.

FIRST EMBODIMENT

Figure 1:
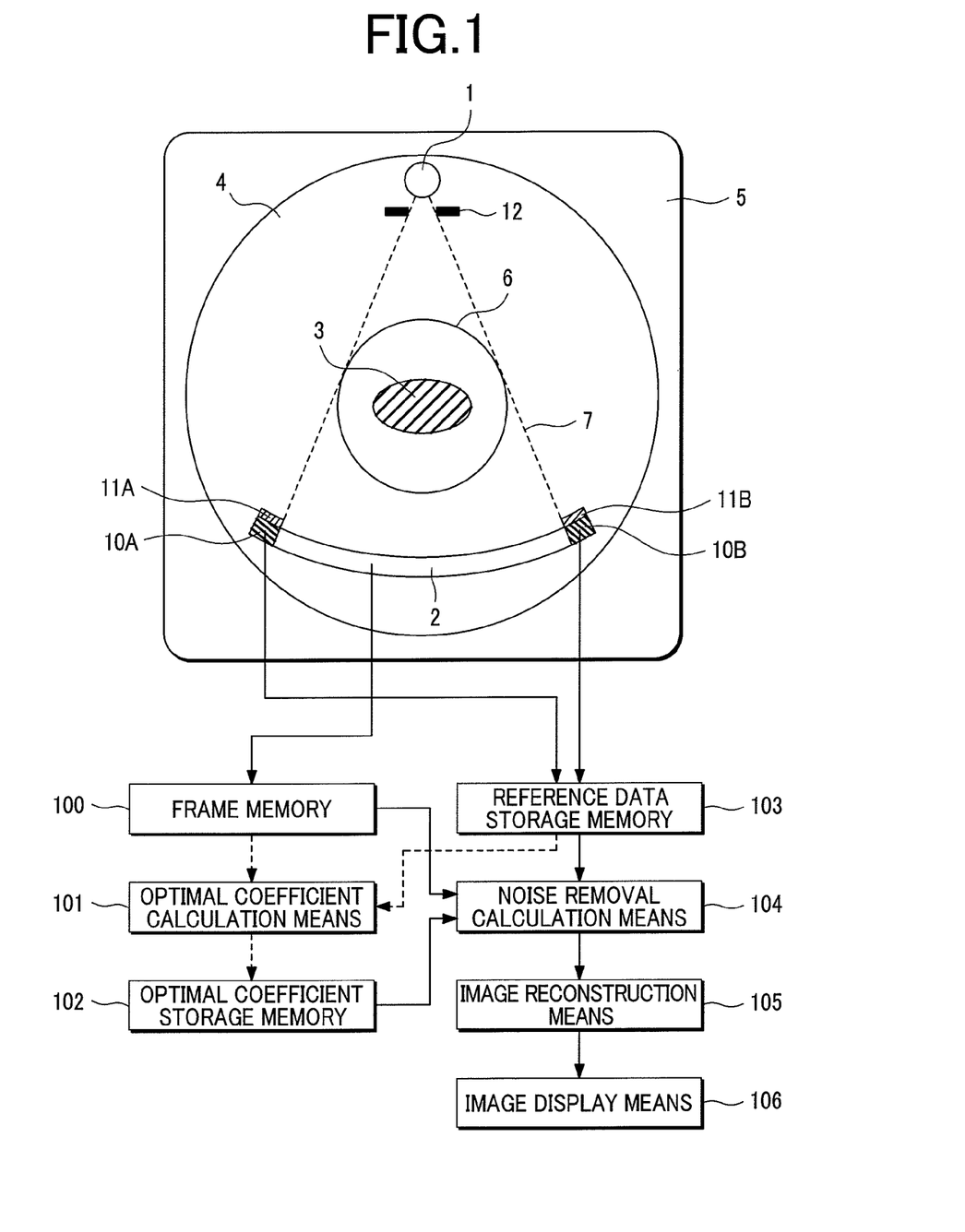
FIG. 1 is an explanatory front view illustratively showing an X-ray imaging device in accordance with a first embodiment of the present invention.

FIG. 1 is a front view illustratively showing an X-ray imaging device in accordance with the first embodiment of the present invention. The first embodiment is supposed to be an X-ray computed tomography (CT) apparatus that is one of applications of the present invention.

The X-ray imaging device in accordance with the first embodiment includes an X-ray source 1, an X-ray detector 2, a rotary panel 4, a gantry 5, reference detectors 10A and 10B, anti-scattering collimators 11A and 11B, an X-ray collimator 12, a frame memory 100, an optimal coefficient calculation means 101, an optical coefficient storage memory 102, a reference data storage memory 103, a noise removal calculation means 104, an image reconstruction means 105, and an image display means 106. Hereinafter, the X-ray source 1 and X-ray detector 2 may be generically referred to as an imaging system.

The imaging system is fixed to the rotary panel 4. The rotary panel 4 and the entire imaging system are stowed in the gantry 5. The gantry 5 has a bore 6, into which a subject 3 is carried, formed in the center thereof. The rotary panel 4 can be rotated within the gantry 5 with an axis, which passes through the center of the bore 6 and is perpendicular to the sheet of the drawing, as an axis of rotation. Incidentally, the rotary panel 4 is rotated by a known driving motor that is not shown. The reference detectors 10A and 10B are located at both ends of the X-ray detector 2 in the direction of a plane of rotation. The X-ray collimator 12 is disposed on the face of the X-ray source 1. The X-ray collimator 12 limits an irradiation range 7 for fear X-rays radiated from the X-ray source 1 may be irradiated to outside a region detectable by the X-ray detector 2. Consequently, X-rays will not be irradiated directly to the reference detectors 10A and 10B. Moreover, the anti-scattering collimators 11A and 11B are disposed on the faces of the reference detectors 10A and 10B respectively for fear X-rays scattered in the subject 3 may fall on the reference detectors 10A and 10B.

Next, the operation of the X-ray imaging device in accordance with the first embodiment will be described below. The X-ray imaging device supports two measurement modes, that is, a radiography mode and an optimal coefficient measurement mode. In FIG. 1, arrows drawn with solid lines indicate flows of data in the radiography mode, and arrows drawn with dashed lines indicate flows of data in the optimal coefficient measurement mode.

The optimal coefficient measurement mode is a measurement mode intended to deduce the aforesaid optimal approximation coefficients. Measurement precedes radiography. For the measurement, the subject 3 is not carried in. Moreover, the X-ray collimator 12 limits the irradiation range 7 so that X-irradiation to the X-ray detector 2 will be entirely blocked. When initiation of measurement is instructed, the rotary panel 4 begins rotating at the same time. Once the rotating velocity of the rotary panel 4 becomes steady-state, X-irradiation from the X-ray source 1 is initiated. At this time, the X-ray detector 2 and the reference detectors 10A and 10B measure electromagnetic noise (external noise) caused by a rotational driving system for the rotary panel 4 or a power source or the like for the X-ray source 1 which is not shown. Data of the external noise detected by the X-ray detector 2 is recorded in the frame memory 100, and data items of the external noises detected by the reference detectors 10A and 10B respectively are recorded in the reference data storage memory 103. The data acquisition is performed during several rotations (normally, five to ten rotations) of the rotary panel 4. When all data items have been acquired, the measurement is terminated and the X-irradiation and the rotation of the rotary panel 4 are ceased. Moreover, when the measurement is terminated, the optimal coefficient calculation means 101 checks the data items recorded in the frame memory 100 and reference data storage memory 103 respectively. The optimal coefficient calculation means 101 then calculates optimal approximation coefficients relevant to the X-ray detector 2 according to a method to be described later, and then records the calculated coefficients in the optimal coefficient storage memory 102.

In the radiography mode, the subject 3 is carried in. Moreover, the X-ray collimator 12 limits the irradiation range 7 to such an extent that X-rays can be irradiated to the whole or part of the X-ray detector 2. When initiation of measurement is instructed, the rotary panel 4 begins rotating at the same time. Once the rotating velocity of the rotary panel 4 becomes steady-state, X-irradiation from the X-ray source 1 is initiated. At this time, the reference detectors 10A and 10B measures external noise. On the other hand, the X-ray detector 2 measures a signal of X-rays transmitted by the subject 3 and the external noise alike. Data of a projection signal detected by the X-ray detector 2 is recorded in the frame memory 100, while data items of the external noises detected by the reference detectors 10A and 10B respectively are recorded in the reference data storage memory 103.

Every time the data is recorded, the noise removal calculation means 104 reads projection signal data from the frame memory 100, external noise data from the reference data storage memory 103, and data of optimal approximation coefficients from the optimal coefficient storage memory 102. The noise removal calculation means 104 performs noise removal calculation on the projection signal data according to a method to be described later. The projection signal data having noise removed therefrom is subjected to known image reconstruction by the image reconstruction means 105, whereby an X-ray tomographic image of the subject 3 is produced. The produced X-ray tomographic image is displayed by the known image display means 106.

Figure 2:
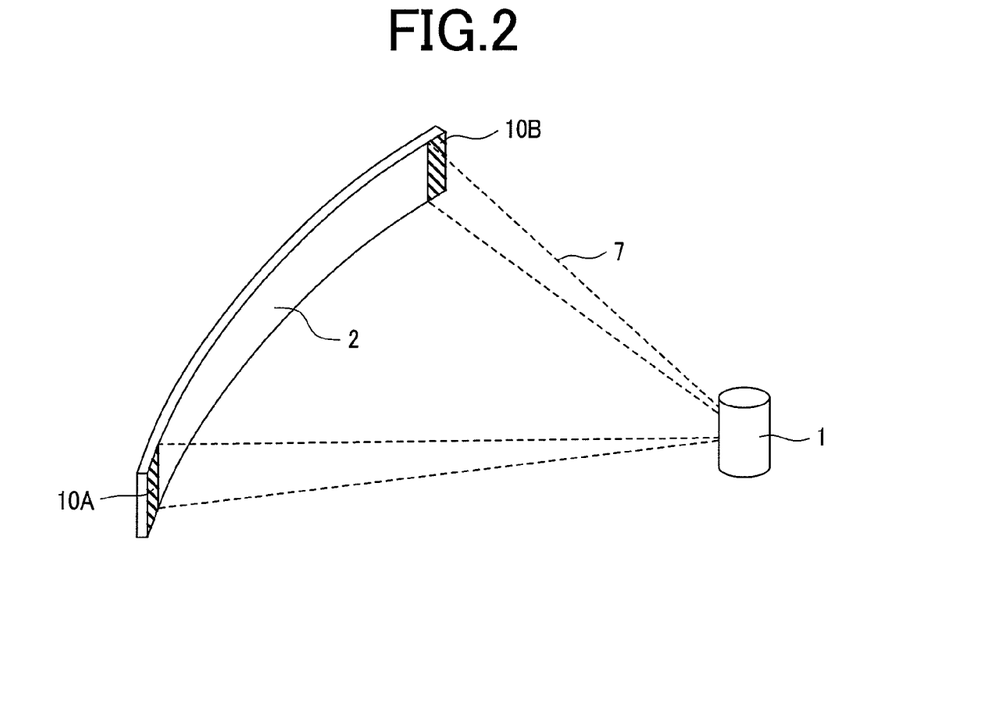
FIG. 2 is an explanatory diagram concerning the arrangement of an X-ray detector and reference detectors which is adapted to the first embodiment.
Figure 3:
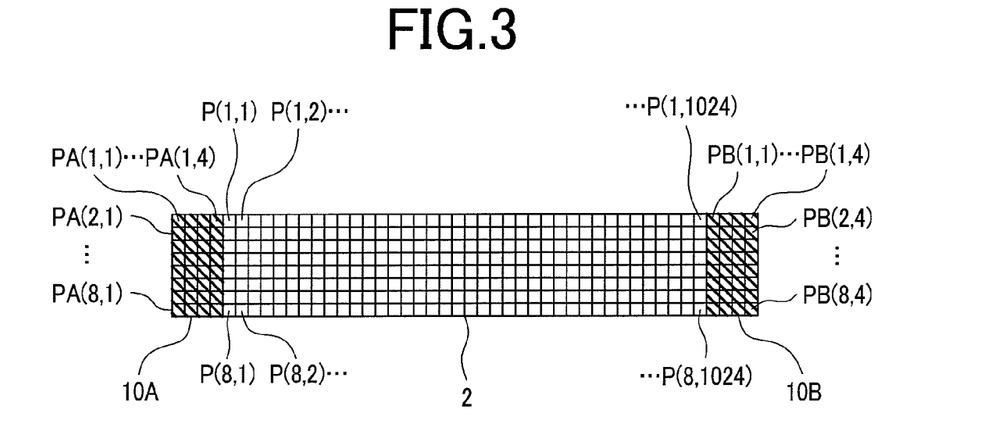
FIG. 3 is an explanatory diagram showing a pixel distribution adapted to the X-ray detector and reference detectors alike included in the first embodiment.

FIG. 2 is an explanatory diagram showing the arrangement of the X-ray detector 2 and the reference detectors 10A and 10B which is adapted to the first embodiment of the present invention. FIG. 3 is an explanatory diagram showing a pixel distribution adapted to the X-ray detector 2 and the reference detectors 10A and 10B alike.

As shown in FIG. 3, the X-ray detector 2 has a multi-slice structure being divided into 1024 portions in the direction of channels (a horizontal direction in FIG. 3) and eight portions in the direction of slices (a vertical direction in FIG. 3). The reference detectors 10A and 10B are disposed at both ends of the X-ray detector 2 in the direction of channels, and divided into four portions in the direction of channels and eight portions in the direction of slices. Incidentally, the number of divisions in the direction of channels or the direction of slices is not limited to the value adopted in the present embodiment. Moreover, the X-ray detector 2 and the reference detectors 10A and 10B may be constructed as an integrated sensor or may be independently constructed and then juxtaposed. As described later, signals measured at thirty-two pixels PA(1,1) to PA(8,4) constituting the reference detector 10A are binned and treated as one signal. Likewise, signals measured at thirty-two pixels PB(1,1) to PB(8,4) constituting the reference detector 10B produced in due course and treated as one signal. Namely, in the present embodiment, the number of reference detectors is 2 (N=2 in the formulae 1 to 5), and the binned signals thereof are treated as the signals $q_1(t)$ and $q_2(t)$ respectively. As mentioned above, since signals detected at multiple pixels are binned, circuit noise (internal noise) generated at each pixel can be reduced. As described later, optimal approximation coefficients $\alpha_1$ and $\alpha_2$ are deduced relative to each of the pixels P(1,1) to P(8,1024) constituting the X-ray detector 2, and stored in the optimal coefficient storage memory 102.

Figure 4:
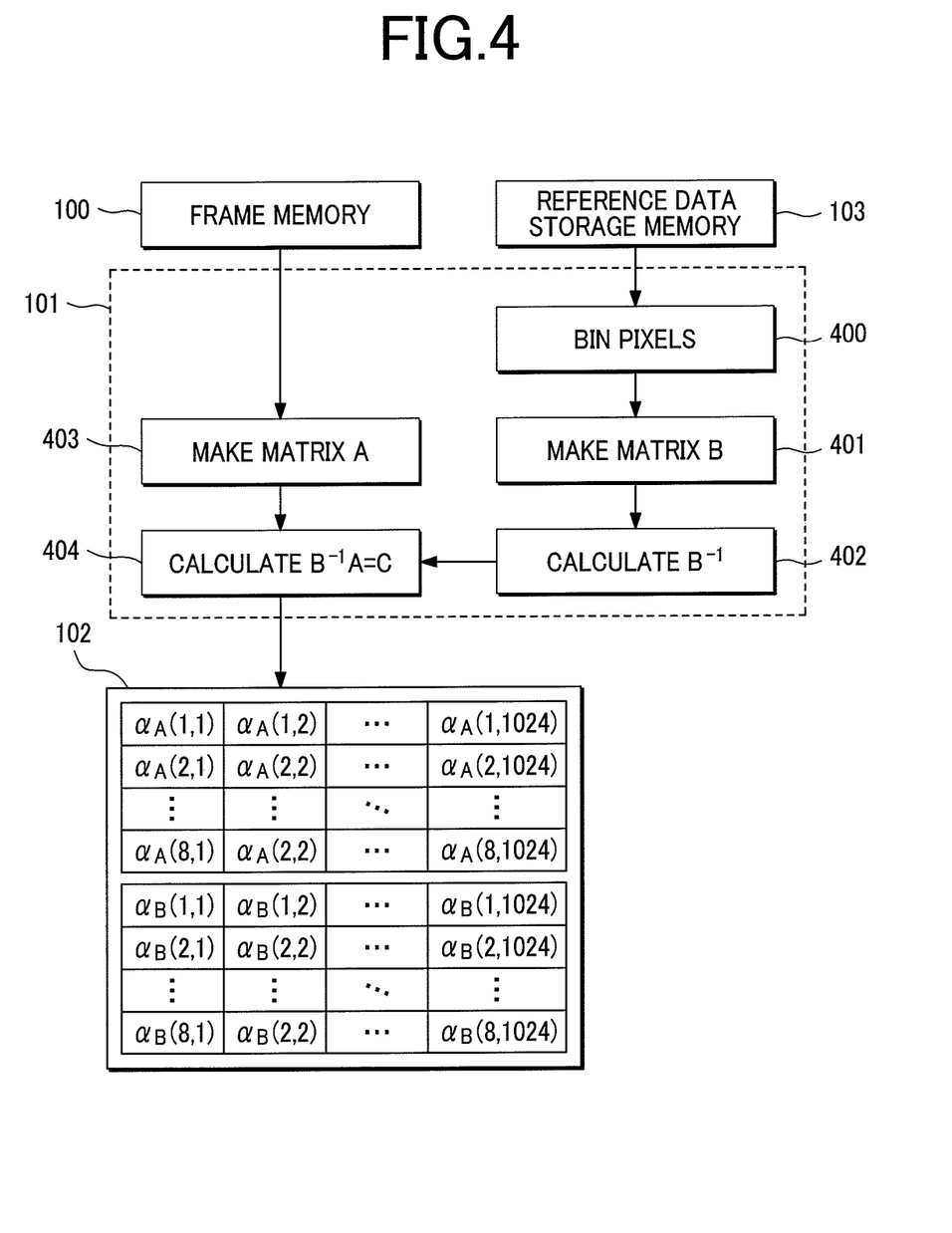
FIG. 4 is an explanatory diagram concerning a procedure to be followed by an optimal coefficient calculation means shown in FIG. 1.

FIG. 4 is an explanatory diagram concerning a procedure to be followed by the optical coefficient calculation means 101.

Processing to be described later and performed by the optimal coefficient calculation means 101 is implemented in software by a dedicated arithmetic unit or a general-purpose arithmetic unit. The optimal coefficient calculation means 101 reads signals PA(1,1) to PA(8,4), which are detected at the respective pixels constituting the reference detector 10A, from the reference data storage memory 103, and bins them to work out binned data $q_1(t)$. Likewise, the optimal coefficient calculation means 101 reads signals PB(1,1) to PB(8,4), which are detected at the respective pixels constituting the reference detector 10B, from the reference data storage memory 103, and bins them to work out binned data $q_2(t)$ (step 400). Thereafter, the optimal coefficient calculation means 101 performs cross-correlation calculation expressed by the formula 4 on the binned data items $q_1(t)$ and $q_2(t)$, and thus produces a matrix B expressed with the first term in the right side of the formula 3 (step 401). Thereafter, the optimal coefficient calculation means 101 uses a known calculation algorithm to produce an inverse matrix $B^{-1}$ of the matrix B (step 402).

Thereafter, data measured by the X-ray detector 2 is read from the frame memory 100 in order to produce a matrix A expressed with the left side of the formula 3 (step 403). Thereafter, a matrix C is calculated as $C=B^{-1}A$, and the optimal approximation coefficients $\alpha_1$ and $\alpha_2$ that are the elements of the matrix C are calculated (step 404). The pieces of processing of steps 403 and 404 are repeatedly executed for each of the pixels P(1,1) to P(8,1024) constituting the X-ray detector 2. The optimal approximation coefficients $\alpha_1$ and $\alpha_2$ calculated relative to each of the pixels are stored in the optimal coefficient storage memory 102. Incidentally, in FIG. 4, $\alpha_A(i,j)$ and $\alpha_B(i,j)$ denote the values $\alpha_1$ and $\alpha_2$ calculated relative to pixels P(i,j).

Figure 5:
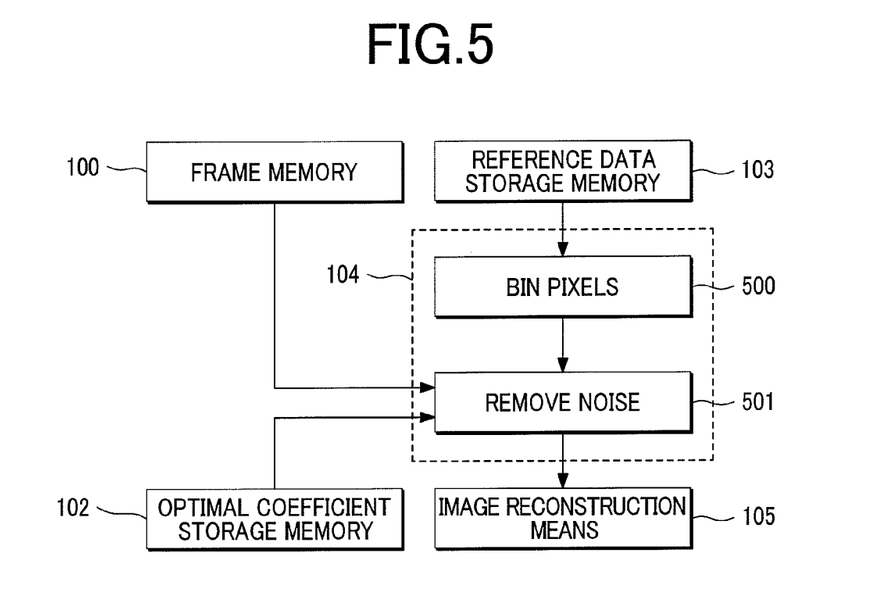
FIG. 5 is an explanatory diagram concerning a procedure to be followed by a noise removal calculation means shown in FIG. 1.

FIG. 5 is an explanatory diagram concerning a procedure to be followed by the noise removal calculation means 104. Processing to be described later and performed by the noise removal calculation means 104 is implemented in software by a dedicated arithmetic unit or a general-purpose arithmetic unit. The noise removal calculation means 104 reads signals PA(1,1) to PA(8,4), which are detected at the respective pixels constituting the reference detector 10A, from the reference data storage memory 103, and bins them to work out binned data $q_1(t)$. Likewise, the noise removal calculation means 104 reads signals PB(1,1) to PB(8,4), which are detected at the respective pixels constituting the reference detector 10B, from the reference data storage memory 103, and bins them to work out binned data $q_2(t)$ (step 500). Thereafter, the noise removal calculation means 104 reads data, which is measured by the X-ray detector 2, from the frame memory 100, and reads the optimal approximation coefficients $\alpha_1$ and $\alpha_2$ associated with each of the pixels. The noise removal calculation means 104 uses the binned data items to perform noise removal calculation expressed by the formula 5 (step 501). The calculation of step 501 is repeatedly executed for each of the pixels P(1,1) to P(8,1024) constituting the X-ray detector 2.

Figure 6:
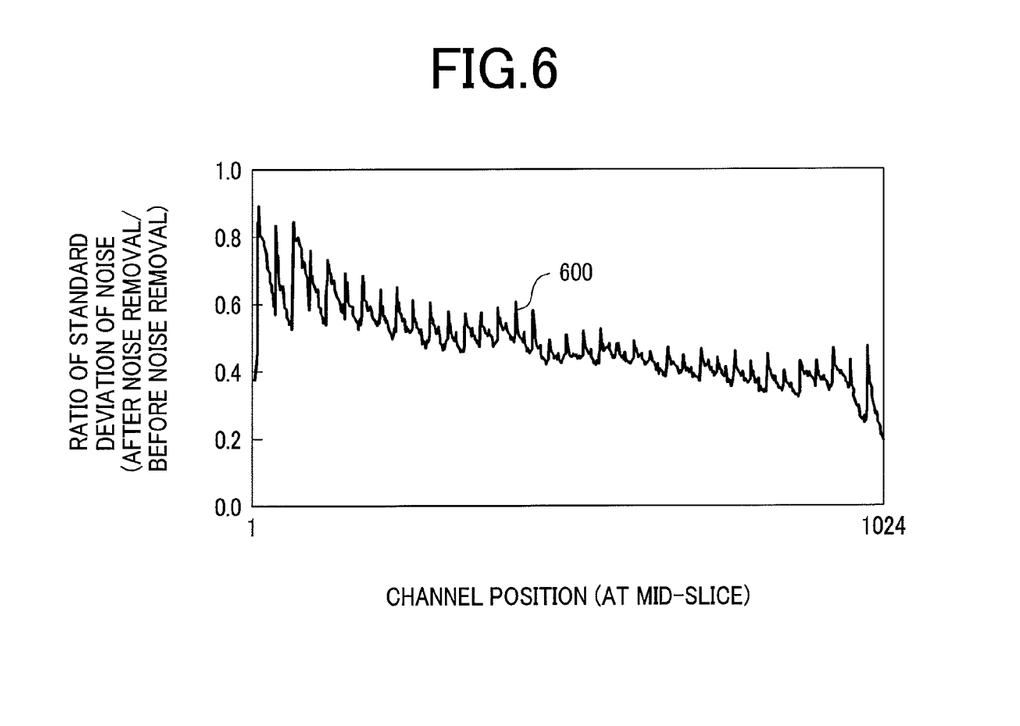
FIG. 6 is an explanatory diagram concerning an effect of noise reduction exerted in the X-ray imaging device in accordance with the first embodiment.

FIG. 6 is an explanatory diagram concerning an effect of noise reduction exerted in the X-ray imaging device in accordance with the first embodiment. A graph 600 shown in FIG. 6 indicates a ratio of a standard deviation of noise detected in the center slice of the X-ray detector 2 (after noise removal to a standard deviation thereof detected therein before noise removal). The graph demonstrates that external noise is efficiently removed and the standard deviation of noise is contracted to about 20% to 80% of the standard deviation detected before noise removal.

Figure 7:
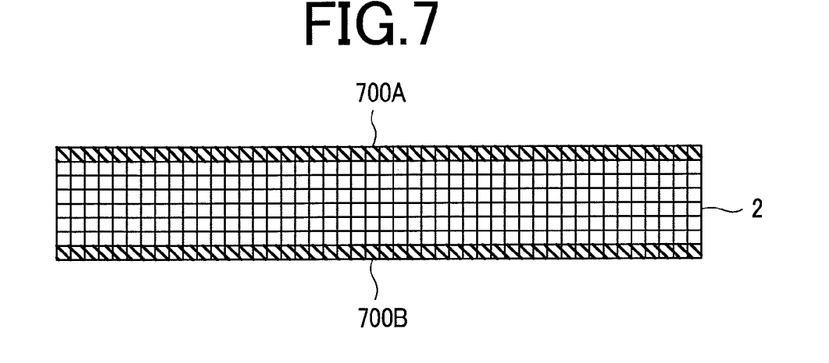
FIG. 7 is an explanatory diagram showing another example of the arrangement of reference detectors to be adapted to the first embodiment.

FIG. 7 is an explanatory diagram showing another example of the arrangement of reference detectors. In this example, reference detectors 700A and 700B are located on both edges of the X-ray detector 2 in the direction of slices thereof.

Similarly to the reference detectors shown in FIG. 3, all pixel values in each of the reference detectors 700A and 700B may be binned and regarded as one signal. The locations of N (N<M) reference pixels designated from among M reference pixels (reference detection elements) constituting each of the reference detectors 700A and 700B may be varied depending on the location of a pixel in the X-ray detector 2 whose data will have noise removed therefrom. In the latter case, if reference pixels located near the pixel whose data will have noise removed therefrom are selected, the correlation of external noise measured in the pixel to external noises measured in the reference pixels will improve. Consequently, the precision in noise removal improves.

Figure 8:
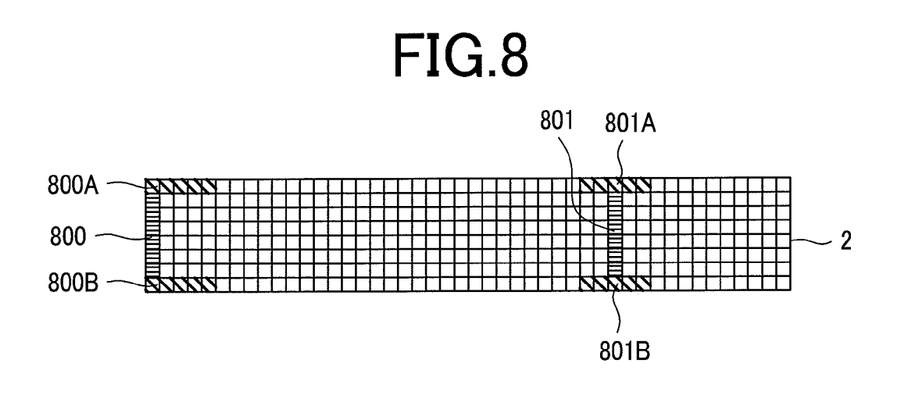
FIG. 8 is an explanatory diagram concerning a method of selecting reference pixels from the reference detectors shown in FIG. 7.

FIG. 8 is an explanatory diagram concerning a method of selecting reference pixels from each of the reference detectors 700A and 700B. In this example, five reference pixels located most closely to a pixel location in the X-ray detector 2 are selected from each of the reference detectors 700A and 700B. For example, relative to a pixel location 800 in the X-ray detector 2, five closest reference pixels 800A and 800B are selected. Relative to a pixel location 801 in the X-ray detector 2, five closest reference pixels 801A and 801B are selected. The values at the five reference pixels are binned and regarded as one reference signal. In this example, five reference pixels are selected. However, the number of pixels to be selected is not limited to five. Moreover, in FIG. 3, FIG. 7, and FIG. 8, two reference detectors (N=2) are employed. However, the number of reference detectors is not limited to two.

Figure 9:
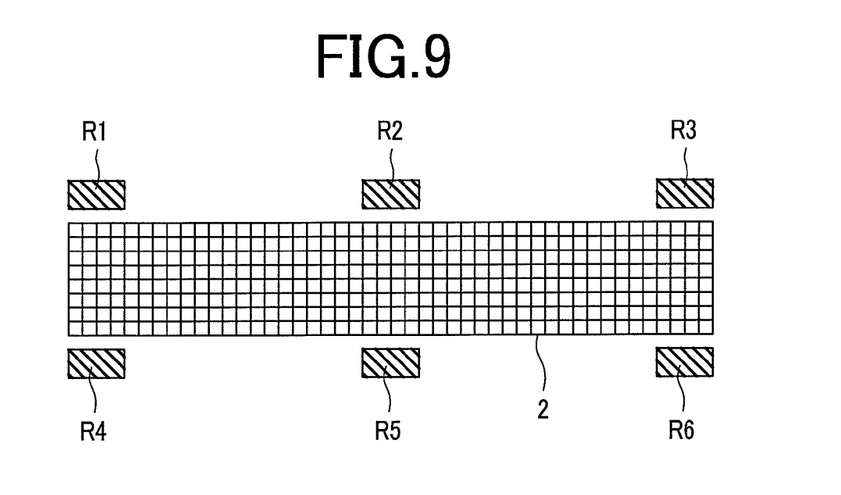
FIG. 9 shows an example of the arrangement of reference detectors R1 to R6 constructed independently of the X-ray detector which is adapted to the first embodiment.

FIG. 9 shows an example of the arrangement of reference detectors R1 to R6 constructed independently of the X-ray detector 2. In this example, since part of pixels constituting the X-ray detector 2 need not be used as reference detectors, a field of view offered for imaging by the X-ray detector 2 can be effectively utilized. For noise removal, all the reference detectors R1 to R6 may be used (N=6), or several reference pixels located most closely to a pixel whose data has noise removed therefrom may be selected and utilized.

The X-ray imaging device in accordance with the first embodiment has been described so far. The present invention is not limited to the first embodiment. Needless to say, the present invention can be modified in various manners without a departure from the gist thereof. For example, in the first embodiment, a multi-slice CT sensor is considered as the X-ray detector 2. Alternatively, the present invention may be applied to a single-slice CT sensor or a two-dimensional X-ray sensor employed in cone-beam CT.

SECOND EMBODIMENT

Figure 10:
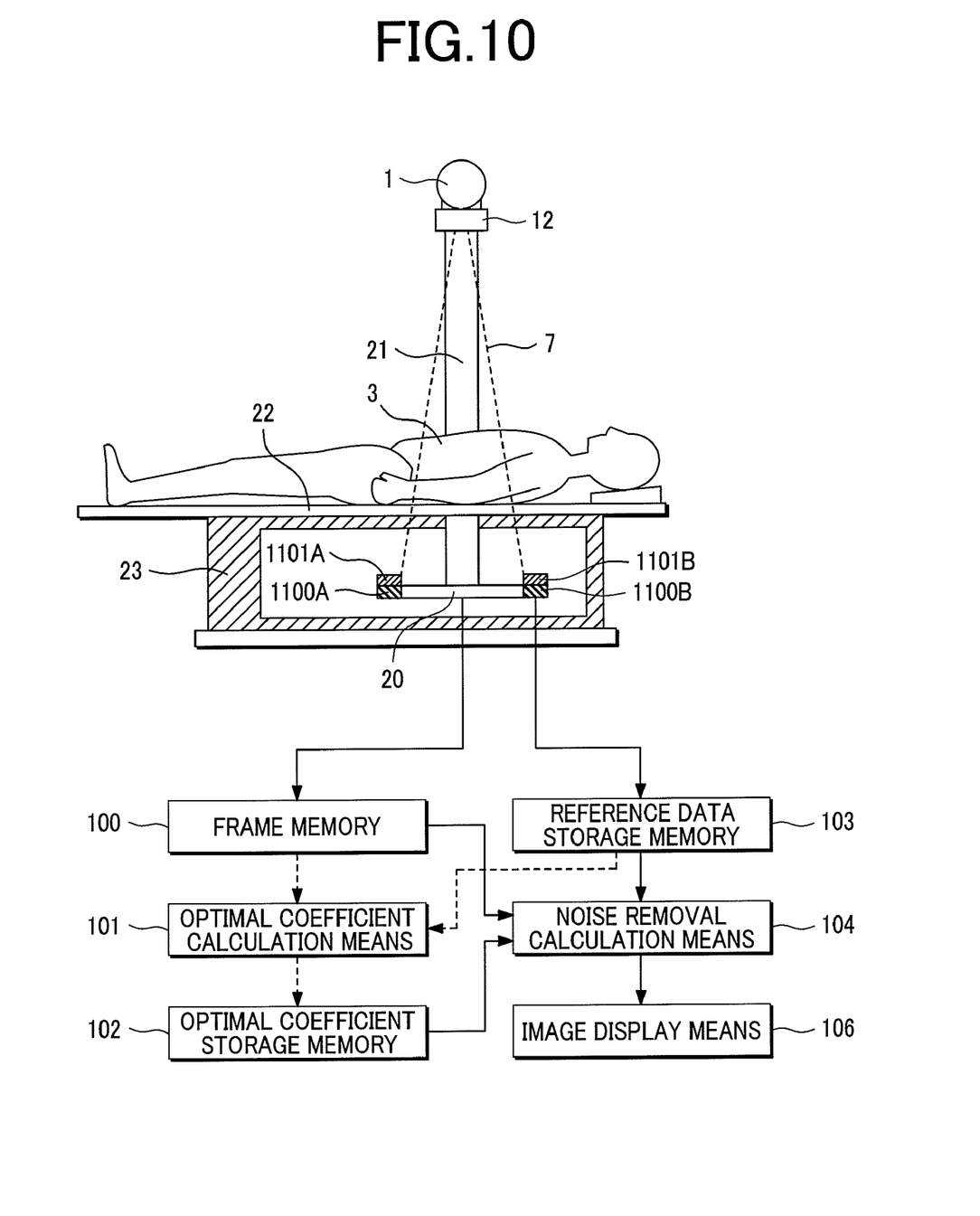
FIG. 10 is an explanatory diagram illustratively showing an X-ray imaging device in accordance with the second embodiment of the present invention.

FIG. 10 illustratively shows an X-ray imaging device in accordance with the second embodiment of the present invention. The second embodiment is supposed to be an X-ray imaging device for diagnostic imaging that is one of applications of the present invention.

The X-ray imaging device in accordance with the second embodiment includes an X-ray source 1, an X-ray detector 2, reference detectors 1100A and 1100B, an X-ray collimator 12, anti-scattering collimators 1101A and 1101B, a support column 21, a tabletop 22, a radiographic table 23, a frame memory 100, an optimal coefficient calculation means 101, an optimal coefficient storage memory 102, a reference data storage memory 103, a noise removal calculation means 104, and an image display means 106. A known X-ray flat panel detector (FPD) is adopted as the X-ray detector 20. The reference detectors 1100A and 1000B are located at both ends of the X-ray detector 20. The X-ray collimator 12 is located on the face of the X-ray source 1. The X-ray collimator 12 limits an irradiation range 7 for fear X-rays radiated from the X-ray source 1 may be irradiated to outside a region detectable by the X-ray detector 20. Consequently, X-rays will not be irradiated directly to the reference detectors 1100A and 1100B.

The anti-scattering collimators 1101A and 1101B are disposed on the faces of the respective reference detectors 1100A and 1000B for fear X-rays scattered in a subject 3 may fall on the reference detectors 1100A and 1100B.

Next, the operation of the X-ray imaging device in accordance with the second embodiment will be described below. The X-ray imaging device supports two measurement modes, that is, a radiography mode and an optimal coefficient measurement mode. In FIG. 10, arrows drawn with solid lines indicate flows of data in the radiography mode, and arrows drawn with dashed lines indicate flows of data in the optimal coefficient measurement mode.

The optimal coefficient measurement mode is the measurement mode intended to deduce optimal approximation coefficients. Measurement precedes radiography. For measurement, the subject 3 is not carried in. The X-ray collimator 12 limits the irradiation range 7 so as to entirely block X-irradiation to the X-ray detector 2. When initiation of measurement is instructed, X-irradiation from the X-ray source 1 is initiated. The X-ray detector 20 and the reference detectors 1100A and 1000B repeatedly measure data of external noise during successive scans. The data of external noise detected by the X-ray detector 20 is recorded in the frame memory 100. The data items of external noises detected by the reference detectors 1100A and 1000B respectively are recorded in the reference data storage memory 103. The data acquisition is performed over several tens to several hundreds of scans. When all data items have been acquired, the measurement is terminated and X-irradiation is ceased. When the measurement is terminated, the optimal coefficient calculation means 101 checks data items recorded in the frame memory 100 and reference data storage memory 103 respectively. The optimal coefficient calculation means 101 then calculates optimal approximation coefficients relevant to the X-ray detector 20 according to the same method as the one described in relation to the first embodiment, and records the calculated coefficients in the optimal coefficient storage memory 102.

In the radiography mode, the subject 3 is carried in. The X-ray collimator 12 limits the irradiation range 7 to such an extent that X-rays can be irradiated to the whole or part of the X-ray detector 20. When initiation of measurement is instructed, X-rays are radiated from the X-ray source 1, and one scan or successive scans are performed. At this time, the reference detectors 1100A and 1100B measure external noise. On the other hand, the X-ray detector 20 measures a signal of X-rays transmitted by the subject 3 and also measures external noise. Data of a projection signal detected by the X-ray detector 20 is recorded in the frame memory 100. The data items of external noises detected by the reference detectors 1100A and 1100B respectively are recorded in the reference data storage memory 103. Every time the data is recorded, the noise removal calculation means 104 reads projection signal data from the frame memory 100, external noise data from the reference data storage memory 103, and data of optimal approximation coefficients from the optimal coefficient storage memory 102, and performs noise removal calculation according to the same method as the one described in relation to the first embodiment. The image data having noise removed therefrom is displayed by the known image display means 106.

Figure 11:
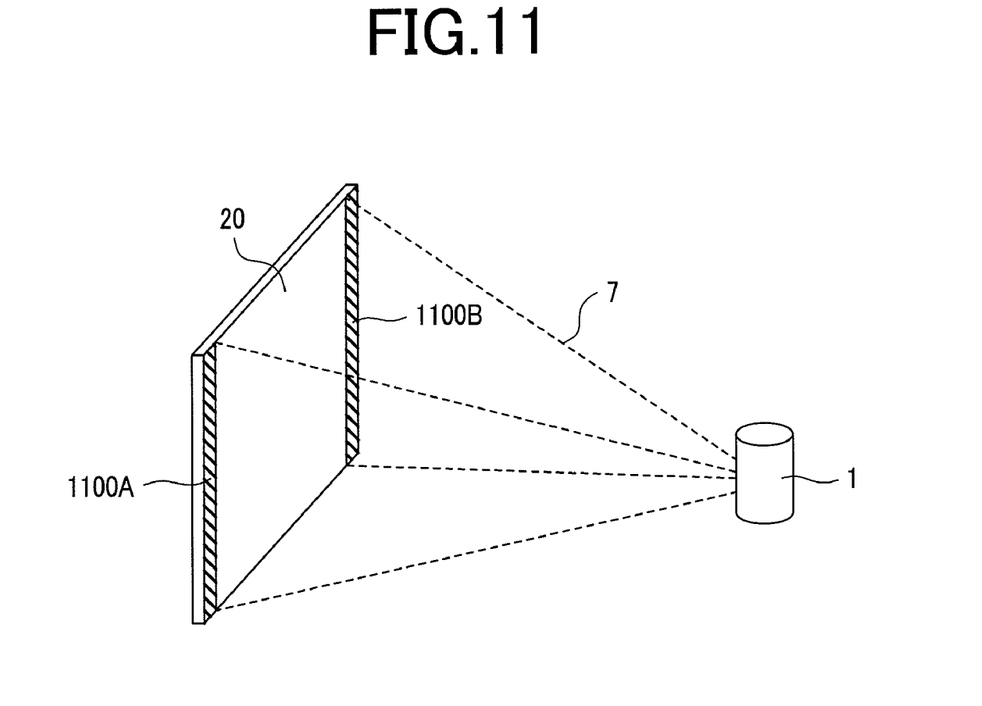
FIG. 11 is an explanatory diagram showing the arrangement of an X-ray detector and reference detectors to be adapted to the second embodiment.
Figure 12:
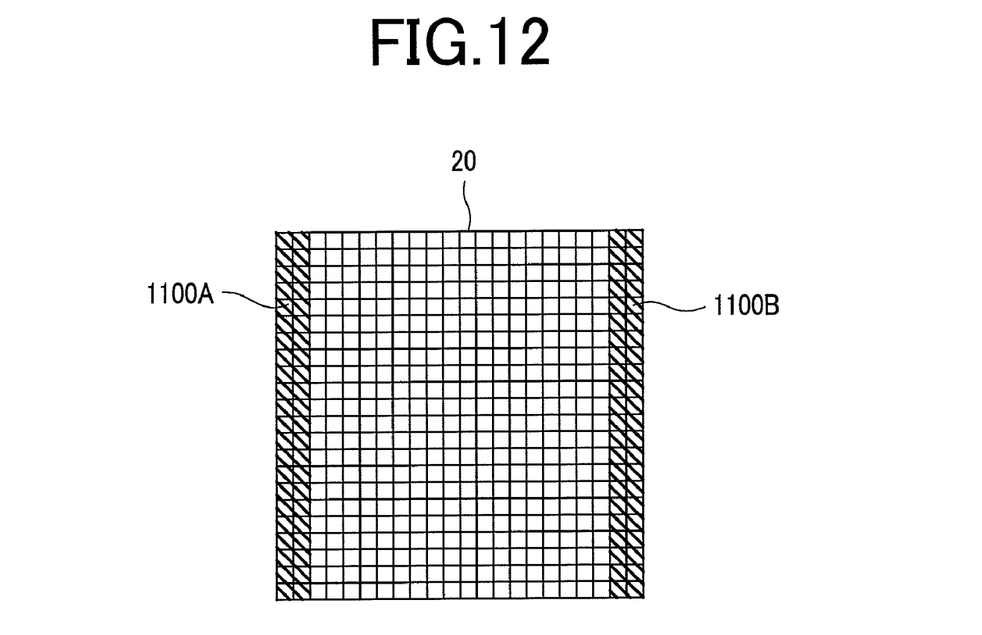
FIG. 12 is an explanatory diagram showing a pixel distribution to be adapted to the X-ray detector and reference detector alike included in the second embodiment.

FIG. 11 is an explanatory diagram showing the arrangement of the X-ray detector and the reference detectors 1100A and 1100B which is adapted to the second embodiment of the present invention. FIG. 12 is an explanatory diagram showing a pixel distribution adapted to the X-ray detector 20 and the reference detectors 1100A and 1100B alike. The numbers of pixel divisions in a horizontal direction and a vertical direction respectively of the X-ray detector 20 are 3068 pixels and 3072 pixels. However, the numbers of pixels are not limited to these values. The reference detectors 1100A and 1100B are located on both edges of the X-ray detector 20 in the horizontal direction thereof. Each of the reference detectors 1100A and 1100B has two pixels juxtaposed in the horizontal direction and 3072 pixels juxtaposed in the vertical direction. However, the numbers of divisions of the reference detectors 1100A and 1100B in the horizontal direction and vertical direction respectively are not limited to the above values.

The X-ray detector 20 and the reference detectors 1100A and 1100B may be constructed as an integrated sensor or may be constructed independently of one another and then juxtaposed. Signal values detected at all the pixels constituting each of the reference detectors 1100A and 1100B may be binned and handled as one signal. Otherwise, the locations of reference pixels in each of the reference detectors 1100A and 1100B may be varied depending on the location of a pixel in the X-ray detector 20 whose data will have noise removed therefrom. In the latter case, reference pixels located near the pixel whose data will have noise removed therefrom are selected. Consequently, the correlation of external noise measured in the pixel to external noises measured in the reference pixels is upgraded. Eventually, the precision in noise removal improves.

Figure 13:
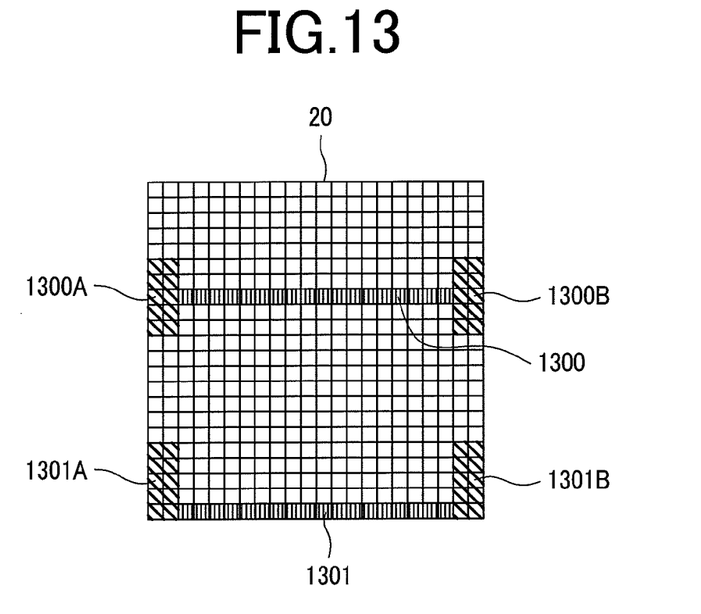
FIG. 13 is an explanatory diagram concerning a method of selecting reference pixels from the reference detectors shown in FIG. 12.

FIG. 13 is an explanatory diagram concerning a method of selecting reference pixels from each of the reference detectors 1100A and 1100B. In this example, ten reference pixels located most closely to a pixel location in the X-ray detector 20 are selected from each of the reference detectors 1100A and 1100B. For example, relative to a pixel location 1300 in the X-ray detector 20, ten closest reference pixels 1300A and 1300B are selected. Relative to a pixel location 1301 in the X-ray detector 20, ten closest reference pixels 1301A and 1301B are selected. The values at the ten reference pixels are binned and regarded as one reference signal. In this example, ten reference pixels are selected. However, the number of pixels to be selected is not limited to ten. In FIG. 12 and FIG. 13, two reference detectors (N=2) are utilized. However, the number of reference detectors is not limited to two.

Figure 14:
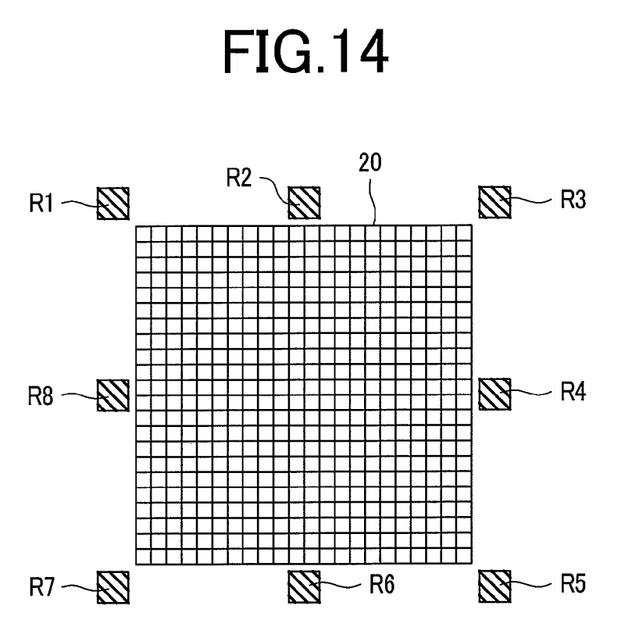
FIG. 14 shows an example of the arrangement of reference detectors R1 to R8 constructed independently of the X-ray detector which is adapted to the second embodiment; and, FIG. 15 shows a typical configuration of an X-ray imaging device to which the present invention is adapted.

FIG. 14 shows an example of the arrangement of reference detectors R1 to R8 constructed independently of the X-ray detector 20. In this example, since part of the pixels constituting the X-ray detector 20 need not be used as reference detectors, a field of view offered for imaging by the X-ray detector 20 can be effectively utilized. Moreover, for noise removal, all of the reference detectors R1 to R8 may be utilized (N=8) or several reference pixels located most closely to a pixel whose data will have noise removed therefrom may be selected and utilized.

The second embodiment has been described by taking for instance an X-ray imaging device for diagnostic imaging. The present invention will not be limited to the second embodiment. Needless to say, the present invention can be modified in various manners without a departure from the gist thereof. For example, although the second embodiment is considered as an X-ray imaging device for diagnostic imaging, the present invention may be applied to an X-ray imaging device for industrial inspection or an X-ray imaging device for security.

INDUSTRIAL APPLICABILITY

As described so far, according to the present invention, an X-ray detector capable of suppressing a decrease in a signal-to-noise ratio derived from external noise in a case where it is hard to intercept electromagnetic-wave noise, and offering a wide dynamic range can be realized, and an X-ray imaging technology employing the X-ray detector can be provided.

REFERENCE NUMERALS

1: X-ray source, 2, 20: X-ray detector, 3: subject, 4: rotary panel, 5: gantry, 6: bore, 7: irradiation range, 10A, 10B, 1100A, 1100B: reference detector, 11A, 11B, 1101A, 1101B: anti-scattering collimator, 12: X-ray collimator, 20: X-ray detector, 21: support column, 22: tabletop, 23: radiographic table, 100: frame memory, 101: optimal coefficient calculation means, 102: optimal coefficient storage memory, 103: reference data storage memory, 104: noise removal calculation means, 105: image reconstruction means, 106: image display means, R1 to R9: reference pixel.

The invention claimed is:

1. An X-ray imaging device including a means for generating X-rays, a limiting collimator that limits an X-irradiation range, and an X-ray detection means for detecting an image of X-rays transmitted by a subject, the X-ray imaging device comprising:
a plurality of pieces of reference signal detection means located at the ends of the X-ray detection means and provided with anti-scattering collimators that intercept X-rays transmitted by the subject and scattered from the subject and that lie on faces of the reference signal detection means side of an X-ray incident direction, the reference signal detection means detecting electromagnetic-wave noise generated externally as external noise;
a reference signal memory means in which the external noise detected by the respective pieces of reference signal detection means is stored as reference signals;
a frame memory means in which projection signal data detected by the X-ray detection means with X-irradiation from the X-ray generation means to the X-ray detection means limited by the limiting collimator is stored; and
a calculation means that calculates a noise removal signal using the stored projection signal data and reference signals.

2. The X-ray imaging device according to claim 1, wherein the calculation means includes:
a first calculation means for calculating optimal coefficients, which are used to remove noise, using a noise detected by the X-ray detection means in a state that the limiting collimator intercepts the X-irradiation from the X-ray generation means and the reference signals stored in the reference signal memory means; and
a second calculation means for calculating the noise removal signal using the optimal coefficients calculated by the first calculation means and the stored projection signal data and reference signals.

3. The X-ray imaging device according to claim 2, wherein the second calculation means calculates a noise removal signal f(t)-p'(t) using the signal f(t) and reference signals $q_n(t)$, which are measured by the X-ray detection means and the pieces of reference signal detection means respectively, and the weight coefficients stored in the memory means.

4. The X-ray imaging device according to claim 2, wherein: the reference signal detection means detects N (where $1 \leq N$) reference signals from an X-ray non-irradiated region; and the first calculation means approximates a noise signal p(t) (where t denotes time), which is detected by the X-ray detection means with X-irradiation to the X-ray detection means substantially blocked by the limiting collimator, using a linear sum, $p'(t) = \alpha_1 q_1(t) + \alpha_2 q_2(t) +$, etc., $+ \alpha_N q_N(t)$, of the N reference signals $q_n(t)$ (where n ranges from 1 to N) detected by the reference signal detection means, and calculates weight coefficients $\alpha_n$ (where n ranges from 1 to N) that minimize the mean squared error of the approximate value.

5. The X-ray imaging device according to claim 1, wherein the pieces of reference signal detection means are realized with part of a plurality of detection elements constituting the X-ray detection means.

6. The X-ray imaging device according to claim 1, wherein the limiting collimator is interposed between the X-ray generation means and the subject, and the anti-scattering collimators are interposed between the subject and the pieces of reference signal detection means.

7. The X-ray imaging device according to claim 1, wherein the reference signal detection means is composed of M (where N<M is established) reference detection elements, and the N reference signals $q_n(t)$ are signals detected by N respective reference detection elements designated in advance.

8. The X-ray imaging device according to claim 7,
wherein part or all of the N reference signals $q_n(t)$ are binned values of signals detected by the plurality of pieces of reference detection elements.

9. The X-ray imaging device according to or claim 7,
wherein a combination of N reference detection elements to be designated relative to each of the detection elements constituting the X-ray detection means can be modified.

10. The X-ray imaging device according to claim 9,
wherein a combination of N reference detection elements located at the shortest distance from one another is designated relative to each of the detection elements constituting the X-ray detection means.

* * * * *